(12) United States Patent
Buechi et al.

(10) Patent No.: US 10,046,135 B2
(45) Date of Patent: Aug. 14, 2018

(54) VENTILATION TUBE SYSTEM

(71) Applicant: Hamilton Bonaduz AG, Bonaduz (CH)

(72) Inventors: Rudolf Buechi, Chur (CH); Reto Frei, Bonaduz (CH); Marc Maeder, Malans (CH); Thomas Granzotto, Igis (CH); Axel Zolkos, Felsberg (CH)

(73) Assignee: Hamilton Medical AG (CH)

( * ) Notice: Subject to any disclaimer, the term of this patent is extended or adjusted under 35 U.S.C. 154(b) by 464 days.

(21) Appl. No.: 14/348,958

(22) PCT Filed: Sep. 27, 2012

(86) PCT No.: PCT/EP2012/069107
§ 371 (c)(1),
(2) Date: Apr. 1, 2014

(87) PCT Pub. No.: WO2013/045563
PCT Pub. Date: Apr. 4, 2013

(65) Prior Publication Data
US 2014/0238397 A1 Aug. 28, 2014

(30) Foreign Application Priority Data
Oct. 1, 2011 (DE) .................... 10 2011 054 131

(51) Int. Cl.
*A61M 16/10* (2006.01)
*A61M 16/08* (2006.01)
*A61M 16/16* (2006.01)

(52) U.S. Cl.
CPC .... *A61M 16/1095* (2014.02); *A61M 16/0816* (2013.01); *A61M 16/0833* (2014.02); *A61M 16/0875* (2013.01); *A61M 16/16* (2013.01); *A61M 16/1075* (2013.01); *A61M 2205/14* (2013.01); *A61M 2205/3368* (2013.01); *A61M 2205/3653* (2013.01)

(58) Field of Classification Search
CPC .......... A61M 16/0816; A61M 16/0875; A61M 16/1075; A61M 16/16; A61M 16/1095;
(Continued)

(56) References Cited

U.S. PATENT DOCUMENTS 5,031,612 A 7/1991 Clementi
5,537,996 A * 7/1996 McPhee ................ A61M 16/10
128/204.17
(Continued)

FOREIGN PATENT DOCUMENTS

DE 60320331 T2 5/2009
DE 102008039137 B3 2/2010
(Continued)

*Primary Examiner* — Todd J Scherbel
*Assistant Examiner* — Elliot S Ruddie
(74) *Attorney, Agent, or Firm* — Jansson Munger McKinley & Kirby Ltd.

(57) ABSTRACT

A ventilation tube system for breathing gas for ventilating patients is provided, the system having a first inhalation tube (1) connectable to a respiratory humidifier (3) and to a Y-piece (5); a second inhalation tube (7) connectable to a respirator (9) and to the respiratory humidifier (3); and an exhalation tube (11) connectable to the respirator (9) and to the Y-piece (5); wherein at least certain portions of the first inhalation tube (1) and the exhalation tube (11) each comprise tube heaters having at least one heating wire (15, 17) wherein each of the tube heaters is controllable by a power supply and control unit inside the respiratory humidifier (3) wherein a power supply line (13) of the tube heater of the exhalation tube (11) starts from a link of the second inhalation tube (7) at the respiratory humidifier (3) and proceeds from there via the second inhalation tube (7) and a connecting element (21) separate from the respirator (9).

18 Claims, 2 Drawing Sheets

(58) Field of Classification Search
CPC .......... A61M 16/0833; A61M 16/0066; A61M 16/108; A61M 16/109; A61M 16/1045; A61M 16/1085; A61M 16/161; A61M 2205/3368; A61M 2205/3653; A61M 2205/14; Y10S 261/31
USPC ............ 128/203.12, 203.26, 203.27, 204.14, 128/204.17; 138/118; 261/DIG. 31
See application file for complete search history.

(56) References Cited

U.S. PATENT DOCUMENTS

| | | | | |
|---|---|---|---|---|
| 5,640,951 | A * | 6/1997 | Huddart | A61M 16/08 128/203.26 |
| 6,078,730 | A * | 6/2000 | Huddart | A61M 16/08 219/536 |
| 8,267,084 | B2 * | 9/2012 | Kwok | A61M 16/0066 128/204.18 |
| 8,631,789 | B2 * | 1/2014 | Virr | A61M 16/0816 128/200.24 |
| 9,278,184 | B2 * | 3/2016 | Sofranko | A61M 16/00 |
| 2006/0283447 | A1 | 12/2006 | Dhuper et al. | |
| 2008/0105257 | A1 | 5/2008 | Klasek et al. | |
| 2010/0043793 | A1 * | 2/2010 | Koulechov | A61M 16/0875 128/204.17 |
| 2011/0023874 | A1 * | 2/2011 | Bath | A61M 16/0066 128/202.22 |

FOREIGN PATENT DOCUMENTS

| EP | 2229973 A2 | 9/2010 |
|---|---|---|
| WO | WO2009022004 A2 | 2/2009 |

* cited by examiner

VENTILATION TUBE SYSTEM

FIELD OF INVENTION

The present invention pertains to a ventilation tube system for ventilating patients with breathing gas and to a ventilation system comprising a respirator, a respiratory humidifier, and a ventilation tube system.

BACKGROUND OF THE INVENTION

When patients are being ventilated mechanically on an intensive-care ward, for example, the patient to be ventilated is connected pneumatically to the respirator by means of a ventilation tube system. Because the breathing gas which is delivered to the patient must be adjusted with respect to temperature and humidity to the physiological needs of the patient, a respiratory humidifier is arranged in the inhalation or inspiration tube to heat and humidify the breathing gas. The breathing gas humidifier comprises a liquid container filled with distilled water in the usual manner; the inhalation gas is conducted through this container, and its moisture content is thus increased.

To prevent moisture from condensing inside the ventilation tube system, the inhalation tube and the expiration or exhalation tube are usually provided with electrical tube heaters, which heat the inhalation and exhalation gas flowing through them during operation. A loop of heating wire, for example, is used, which is integrated into the interior of the inhalation or exhalation tube, or the inhalation or exhalation tube is wrapped in each case with a coil of heating wire.

The breathing gas temperature is usually regulated by means of a temperature sensor arranged near the patient; this sensor is connected by an electrical measurement line to a control unit, which is arranged in, for example, the respiratory humidifier.

Ventilation tube systems of this type are known from, for example, DE 10 2008 039 137 B3; DE 10 2007 003 455 A1; DE 44 41 480 A1; and EP 1 338 297 A1. The disadvantage of these ventilation tube systems according to the prior art is that, in addition to the pneumatic connections of the inhalation and exhalation tubes to the respirator, respiratory humidifier, and the Y-piece on the patient, it is also necessary to connect the electrical lines for the tube heater and the temperature sensor, which are present as loose, independent cables and which must be connected independently of each other. The large number of cables and tubes to be connected leads to a loss of time and to the possible confusion of the operator; it also increases the clutter in the patient environment, and the various components are also vulnerable to damage. The use of such loose cables also carries with it the danger that the operator or the patient could become tangled up in them, which, in the worst possible case, could result in the breaking-off of the electrical connection between the respiratory humidifier and the heating wires during the treatment of the patient.

It is therefore the object of the present invention to provide a ventilation tube system which minimizes the number of tubes and electrical lines and their connections, provides a variety of possible ways in which connections can be established, and facilitates establishing both the pneumatic and electrical connections in a single connection procedure.

This object is achieved by the features of claim 1. Advantageous elaborations and embodiments are the object of the subclaims.

SUMMARY OF THE INVENTION

According to an aspect of the invention, a ventilation tube system for breathing gas for ventilating patients is provided, the system having
a first inhalation tube connectable to a respiratory humidifier and to a Y-piece;
a second inhalation tube connectable to the respirator and to the respiratory humidifier; and
an exhalation tube connectable to the respirator and to the Y-piece;
wherein at least certain portions of the first inhalation tube and the exhalation tube each comprise tube heaters having at least one heating wire, wherein each of the tube heaters is controllable by a power supply and control unit inside the respiratory humidifier. The ventilation tube system is characterized in that a power supply line for the tube heater of the exhalation tube starts from a link of the second inhalation tube at the respiratory humidifier and proceeds from there via the second inhalation tube and a connecting element separate from the respirator. As a result of the high degree of integration of the electrical lines into the pneumatic tube connections, the ergonomics are significantly improved for the user, for the possibility of operator error and technical defects is reduced. In addition, fewer tubes and cables are exposed, as a result of which the overall system takes up less space and is less vulnerable to malfunction.

The second inhalation tube preferably has a connecting piece, and the first inhalation tube preferably has one, too; each of these connecting pieces are connectable to the respiratory humidifier in such a way that the pneumatic connection of the breathing gas pathway and the electrical connection are effected together, i.e., essentially simultaneously established or by a single connection procedure. This reduces the susceptibility to error and increases the user-friendliness of the overall system even more, for the pneumatic connections no longer have to be established separately from the electrical connections.

It is advantageous for the connecting element to be designed or formed as a flexible bridge connecting the exhalation tube and the second inhalation tube in the area of the ends facing the respirator, that is, at the ends which can be connected to the respirator. This makes it possible to avoid a connecting element in the form of an exposed cable connection, which has the potential for causing problems, and this in turn increases the user-friendliness.

It is also advantageous for the connecting element to comprise at least two electrical lines. This creates not only the possibility of controlling the tube heater of the exhalation tube from the respiratory humidifier but also of installing measurement or data lines in the exhalation tube for one or more temperature sensors, for example.

The exhalation tube preferably comprises a first connecting piece for connecting to the respirator, and the second inhalation tube preferably comprises a second connecting piece for connecting to the respirator, wherein the connecting element is connected to the first and second connecting pieces. As the connecting pieces to the respirator are usually solid, extruded plastic elements, a strong integral structure is thus created, which is less susceptible to breakdowns and malfunctions. The connecting element can preferably comprise two plug elements, which are insertable into socket elements provided for the purpose on the first and second connecting pieces. The connection between the plug elements and the first and second connecting elements is preferably not detachable, so that the operator has no opportunity of interfering with the electrical connections.

The connecting piece is preferably formed or designed in the shape of a "U". This represents an ergonomic design and corresponds essentially to the path along which the heating, data or measurement lines on the exhalation tube and the second inhalation tube extend.

It is also advantageous for at least certain portions of the heating wire of the tube heater to be formed as a heating coil. The heating coil is integrated into the outside wall of the ventilation tubes, for example, and thus ensures effective heating.

It is especially preferable for the first inhalation tube and/or the second inhalation tube to comprise at least one electrical measurement or data line. This makes it possible for data to be transmitted from the respirator via the electrical data line to the respiratory humidifier and onward to the patient, for example, so that the information can be displayed on the display unit of the respiratory humidifier. Data which have been recorded at the Y-piece, near the patient or from the patient, can be transmitted to the respiratory humidifier or to the respirator. Since the electrical measurement or data lines are formed or designed as integral parts of the pneumatic tube elements, being integrated, for example, into the tube sheathing, there are no exposed electrical cables which could interfere with surrounding activities or be damaged.

In the same way it is advantageous for the exhalation tube to comprise at least one electrical measurement or data line, which continues along the second inhalation tube and the connecting element. As a result, measurement signals from sensors or other data acquired in the exhalation tube can be sent via the connecting element to the respiratory humidifier, where they can be evaluated and displayed.

It is also conceivable as well as advantageous for the electrical measurement or data line of the first inhalation tube to comprise a temperature sensor. The temperature sensor is normally installed very close to the Y-piece, so that it can measure the temperature conditions close to the patient. In this regard it is conceivable that the temperature measurement line or some other line could pass via a connecting piece into the Y-piece, in order to be available for transmissions of measurement or data signals originating from the patient.

It is advantageous for the electrical resistances of the electrical lines in the second inhalation tube, in the exhalation tube, and in the connecting element to be different. The lines in the second inhalation tube and in the connecting element, for example, can be designed as electrical feed lines for the tube heater of the exhalation tube, in such a way as to optimize, for example, the heat output in the exhalation tube and the power consumption. This also increases the reliability of the measurements and of the tube heating function.

It is especially preferable for the ventilation tube system to be designed as a medical-grade, single-use/disposable article. Alternatively, the ventilation tube system can also be designed so that it is medically reusable. To avoid contamination and thus to reduce the danger of infection for patients, most medical-grade consumables are designed as single-use/disposable articles. The ventilation tube system of the present invention also belongs to this class and is used preferably for only one patient and only for a certain period of time. It is also possible, however, for cost or other reasons, to design the ventilation tube system so that it is reusable, meaning that the ventilation tube system can be mechanically cleaned and/or autoclaved, so that it can be put back into service again.

Also according to an aspect of the invention is a ventilation system comprising a respirator, a respiratory humidifier, and a ventilation tube system as described above, wherein the respiratory humidifier comprises a control unit serving to supply the current and to control the tube heaters for the exhalation tube and the first inhalation tube. As previously mentioned, the humidity and the temperature of the breathing gas are usually adjusted by the respiratory humidifier. This offers the advantage to the user that any suitable respirator can be used to make the breathing gas available, and the function of breathing air humidification and its control can take place in the respiratory humidifier, independently of the respirator.

In other words, the ventilation tube system according to the invention can be combined with any existing respirator equipped with the conventional, standardized tube connections for the inhalation and exhalation tubes.

BRIEF DESCRIPTION OF THE DRAWINGS

The invention is to be explained below on the basis of exemplary embodiments with reference to the attached figures.

DETAILED DESCRIPTION

Figure 1:
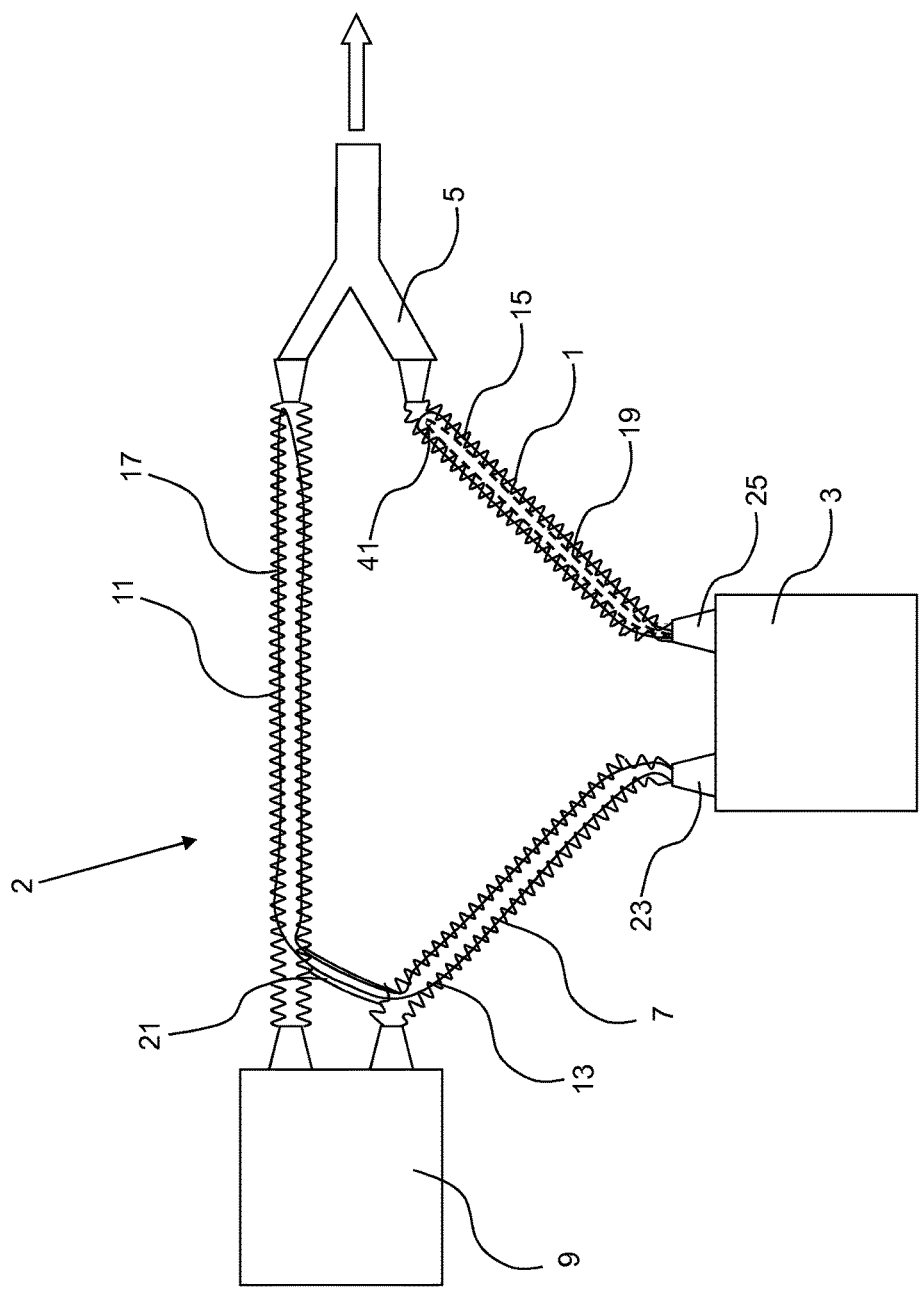
FIG. 1 shows a schematic diagram of a preferred embodiment of the ventilation tube system according to the present invention.

FIG. 1 shows a schematic diagram of a preferred embodiment of an ventilation tube system according to the invention. A first inhalation tube 1 is arranged between a respiratory humidifier 3 and a Y-piece 5. The simply designed end of the Y-piece 5 is directed toward the patient to be ventilated, as indicated by the arrow. A second inhalation tube 7 connects the respiratory humidifier 3 to the respirator 9. Finally, an exhalation tube 11 is arranged between the respirator 9 and the remaining end of the Y-piece 5.

Dry breathing gas is produced in the respirator 9 by, for example, a blower (not shown) and leaves through the second inhalation tube 7, proceeding toward the respiratory humidifier 3. There the breathing gas is conducted in the known manner into a liquid container 31 (not shown in FIG. 1), where it is heated and humidified by the heated liquid. The heated and humidified breathing gas leaves the breathing gas humidifier through the first inhalation tube and reaches the patient through the Y-piece 5.

In correspondence with the breathing cycle controlled by the respirator 9, the spent breathing air leaves the patient again, enters the exhalation tube 11 at the Y-piece 5, and flows back to the respirator 9.

A heating wire 15 is integrated into the wall of the first inhalation tube 1; this wire is designed as a spiral-shaped heating coil. The power supply and the control of the heating wire 15 are handled by the power supply and control unit (not shown) in the respiratory humidifier 3 by way of electrical connections in the first connecting piece 25, which connects the first inhalation tube 1 to the respiratory humidifier 3 or, more precisely, to the liquid container 31 (not shown in FIG. 1). Also integrated into the first inhalation tube 1 is an electrical measurement line 19, which transmits the signal from a temperature sensor 41, arranged on the end near the Y-piece 5, to the control unit (not shown) of the respiratory humidifier 3. The location of the temperature sensor 41 is selected so that it is as close as possible to the patient and yet still a part of the ventilation tube system, which is designed to be replaced as easily as possible. The electrical measurement line 19 is also connected by contact elements from the first connecting piece 25 to corresponding mating contacts on the respiratory humidifier 3 or its liquid container.

The exhalation tube 11 also comprises a tube heater in the form of a heating wire 17, which also is designed as a spiral-shaped heating coil. The reason for heating the exhalation tube 11 is to prevent backflowing breathing gas from condensing in the exhalation tube 11 and from returning in the form of contaminated liquid, for example, to the patient via the Y-piece 5. The tube heater of the exhalation tube 11 can be designed as a continuous unit or in sections. The heating wire 17 is supplied with current over a power supply line 13, which starts from the respiratory humidifier 3, passes through a second connecting piece 23, the second inhalation tube 7, and the connecting element 21, and finally arrives at the exhalation tube 11, where it is connected to the heating wire 17. Leading the power supply line 13 via the second inhalation tube 7 and the connecting element 21 prevents the line supplying power to the exhalation tube 11 from being a freely exposed cable. The power supply line 13 and/or the heating wire 17 can thus be very easily replaced together with the entire ventilation tube system as a single-use article, because neither the one nor the other has to be connected to any other device such as, for example, the respirator.

In FIG. 1, the connecting element 21 is arranged close to the connecting pieces between the respirator 9 and the two tubes, i.e., the second inhalation tube 7 and the exhalation tube 11. The connecting element 21 will now be described in detail referring to FIG. 2.

Figure 2:
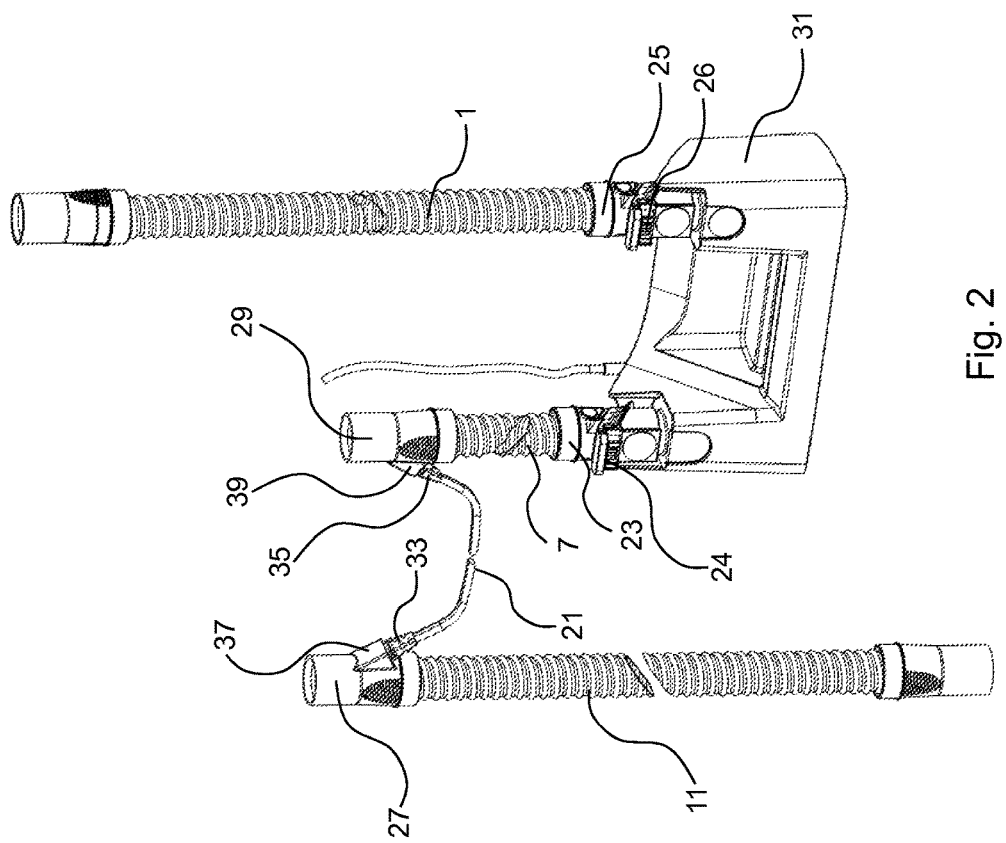
FIG. 2 shows a perspective view of another preferred embodiment of the ventilation tube system according to the present invention.

FIG. 2 shows a perspective view of the ventilation tube system according to the invention, wherein the first and second inhalation tubes 1, 7 are connected by corresponding connecting pieces 23, 25 to the liquid container 31 of the respiratory humidifier 3 (not shown in FIG. 2). FIG. 2 shows only the pneumatic connection between the first and second inhalation tubes 1, 7 and the liquid container 31 via the connecting pieces 23, 25, because the electrical connection of all the electrical lines passing through tubing is established by way of contact elements 24, 26, which are integrated into the connecting pieces 23, 25 and establish the electrical contact with corresponding, mating contact element parts on the housing of the respiratory humidifier 3.

The Y-piece 5 is not shown in FIG. 2 either. Instead, the diagram of FIG. 2 focuses on the elements which in the normal case are medical-grade single-use/disposable articles and which form the necessary replaceable accessories for the function of the respiratory humidifier 3 in conjunction with the ventilation tube system.

Because the essential elements have already been described with respect to FIG. 1, there is no need to describe them again here. The differences versus the embodiment of FIG. 1, which is illustrated only schematically, will be discussed in detail, however.

The material for the tubing, that is, for the first inhalation tube 1, the second inhalation tube 7, and the exhalation tube 11, is formed by a suitable plastic material such as polyethylene or polypropylene. Other suitable materials are also possible. The tubes are extruded or coextruded by known technology. The inside diameter of the tubes will usually be approximately 19 mm for a ventilation system for adults, but smaller diameters such as 12 mm or 15 mm can also be used for ventilation systems for intensive-care stations for children or infants, for example. The connecting pieces, which form the transition between the tubes of the corresponding devices and the Y-piece 5 are also of extruded plastic material. Because, in the medical area, strict requirements are imposed on materials, these materials must comply with ISO standard 5367-2000. As previously mentioned, the ventilation tube system according to the invention is designed either as a medical grade single-use/disposable article or alternatively as a reusable medical article, which can be returned to a usable state again by washing and autoclaving. All components of the ventilation tube system must also be designed in such a way that that they contain no harmful materials, for example, and can withstand a cold disinfectant such as CIDEX, Sekusept, Korsolex, etc.

The connecting element 21 (connecting element is shown in a U-shaped embodiment as reference number 21 in FIG. 2) in the embodiment shown in FIG. 2 is a flexible bridge arranged near the respirator 9 but still separate from it, wherein the second inhalation tube is connected electrically to the exhalation tube by way of this bridge. The length of the flexible bridge is in the range between about 5 cm and about 50 cm; it is preferably about 10 cm long. The connecting piece 29 of the second inhalation tube 7 comprises, near the pneumatic opening, a socket element 39, into which a corresponding plug element 35 of the connecting element 21 is permanently plugged. In the same way, the connecting piece 27 of the exhalation tube 11 comprises, next to the pneumatic opening, a socket element 37, into which the plug element 33 of the connecting element 21 is permanently plugged. The term "permanently" in this context is to be understood as meaning that an operator cannot easily separate the electrical connections between the connecting element 21 and the connecting pieces 27, 29.

The connecting element 21 can comprise several electrical lines, not just two as shown in the exemplary embodiment according to FIG. 1, where only the power supply lines for the heating wire of the exhalation tube 11 are present. For example, additional heating functions for sensors, filters, and the like or other sensors can be connected electrically. It is also possible for signals to be transmitted between the exhalation tube 11 and the respiratory humidifier 3 by way of the connecting element 21. The connecting element 21 between the second inhalation tube 7 and the exhalation tube 11 can be designed in such a way that a lateral displacement between the ends of the two tubes is readily possible, but also so that it is very difficult to rotate them with respect to each other.

With the subject matter of the present invention, a ventilation tube system has been provided which minimizes the number of tubes and electrical lines and their connections, offers a variety of ways in which the connections can be established, and enables effecting the pneumatic and electrical connections in a single connection procedure, without the danger of the operator or the patient becoming tangled up in additional electrical lines for the heating wires and of breaking their electrical connection.

The invention claimed is:

1. A ventilation tube system for breathing gas for ventilating patients comprising: a first inhalation tube pneumatically connectable to a respiratory humidifier and to a Y-piece; a second inhalation tube pneumatically connectable to a respirator and to the respiratory humidifier, the second inhalation tube and the first inhalation tube each comprising a humidifier-connecting piece connectable to the respiratory humidifier, each humidifier-connecting piece including integration of electrical lines for electrical connection between the respective inhalation tube and respiratory humidifier for concurrent electrical and pneumatic connection; an exhalation tube connectable to the respirator and to the Y-piece, at least certain portions of the exhalation tube and the first inhalation tube each including tube heaters having at least one heating wire, each of the tube heaters being controllable by a power supply and control unit inside the respiratory humidifier; and a power supply line for the exhalation-tube heater, wherein such power supply line starts from the respiratory humidifier at the humidifier-connecting piece of the second inhalation tubs continues therefrom along the second inhalation tube to a connecting element, and passes through the connecting element to the heating wire of the exhalation tube, wherein the connecting element is separable from the respirator and forms a bridge element extending between the second inhalation tube and the exhalation tube adjacent to the respirator.

2. The ventilation tube system according to claim 1 wherein the connecting element is formed as a flexible bridge.

3. The ventilation tube system according to claim 1 wherein the connecting element comprises at least two electrical lines.

4. The ventilation tube system according to claim 1 wherein the exhalation tube comprises a first respirator-connecting piece connectable to the respirator, and the second inhalation tube comprises a second respirator-connecting piece connectable to the respirator, wherein the connecting element is connected to the first and second respirator-connecting pieces.

5. The ventilation tube system according to claim 4 wherein the connecting element comprises two plug elements which are insertable into socket elements provided on the first and second respirator-connecting pieces.

6. The ventilation tube system according to claim 5 wherein the connections between the plug elements and the first and second respirator-connecting pieces are lockable.

7. The ventilation tube system according to claim 1 wherein the connecting element is U-shaped.

8. The ventilation tube system according to claim 1 wherein at least certain portions of the heating wire of the tube heater are heating coils.

9. The ventilation tube system according to claim 1 wherein the first inhalation tube and/or the second inhalation tube comprise at least one electrical measurement or data line.

10. The ventilation tube system according to claim 9 wherein the exhalation tube comprises at least one electrical measurement or data line which continues along the second inhalation tube and the connecting element.

11. The ventilation tube system according to claim 9 wherein the electrical measurement or data line is connectable to the respirator.

12. The ventilation tube system according to claim 9 wherein the electrical measurement or data line of the first inhalation tube comprises a temperature sensor.

13. The ventilation tube system according to claim 1 wherein the electrical resistances of the electrical lines in the second inhalation tube, the exhalation tube, and the connecting element are different.

14. The ventilation tube system according to claim 1 formed as a medical-grade single-use or disposable article.

15. The ventilation tube system according to claim 1 wherein the connecting element comprises:
    a first respirator-connecting piece on the second inhalation tube;
    a second respirator-connecting piece on the exhalation tube; and
    an electrical line extending between the first and second respirator-connecting pieces.

16. In a ventilation system including a respirator, a respiratory humidifier, and a ventilation tube system, the improvement wherein the ventilation tube system comprises: a first inhalation tube pneumatically connectable to a respiratory humidifier and to a Y-piece: a second inhalation tube pneumatically connectable to a respirator and to the respiratory humidifier, the second inhalation tube and the first inhalation tube each comprising a humidifier-connecting piece connectable to the respiratory humidifier, each humidifier-connecting piece including integration of electrical lines for electrical connection between the respective inhalation tube and respiratory humidifier for concurrent electrical and pneumatic connection: an exhalation tube connectable to the respirator and to the Y-piece, at least certain portions of the exhalation tube and the first inhalation tube each including tube heaters having at least one heating wire, each of the tube heaters being controllable by a power supply and control unit inside the respiratory humidifier; and a power supply line for the exhalation-tube heater, wherein such power supply line starts from the respiratory humidifier at the humidifier-connecting piece of the second inhalation tube continues therefrom along the second inhalation tube to a connecting element, and passes through the connecting element to the heating wire of the exhalation tube, wherein the connecting element is separate separable from the respirator and forms a bridge element extending between the second inhalation tube and the exhalation tube adjacent to the respirator.

17. The ventilation system of claim 16 wherein the respiratory humidifier comprises a control unit serving to supply power to and to control the tube heaters for the exhalation tube and the first inhalation tube.

18. The ventilation system according to claim 16 wherein the connecting element comprises:
    a first respirator-connecting piece on the second inhalation tube;
    a second respirator-connecting piece on the exhalation tube; and
    an electrical line extending between the first and second respirator-connecting pieces.

* * * * *

UNITED STATES PATENT AND TRADEMARK OFFICE
CERTIFICATE OF CORRECTION

PATENT NO. : 10,046,135 B2
APPLICATION NO. : 14/348958
DATED : August 14, 2018
INVENTOR(S) : Rudolf Buechi et al.

Page 1 of 1

It is certified that error appears in the above-identified patent and that said Letters Patent is hereby corrected as shown below:

In the Claims

At Column 7, Line 13, in Claim 1, delete "tub" and insert -- tube, --.
At Column 8, Line 36, in Claim 16, insert -- , -- after the word tube.
At Column 8, Line 39, in Claim 16, delete "separate".

Signed and Sealed this
Fourth Day of December, 2018

Andrei Iancu
*Director of the United States Patent and Trademark Office*